(12) United States Patent
Amson et al.

(10) Patent No.: US 6,921,845 B1
(45) Date of Patent: Jul. 26, 2005

(54) USE OF ANIMAL MODEL DEFICIENT IN P53 AND HAVING MEMORY DEFICIENCY AND/OR BEHAVIORAL DISORDERS FOR THERAPEUTIC PURPOSES

(75) Inventors: Robert Amson, Paris (FR); Jean-Michel Lassalle, Montbrun-Lauragais (FR); Adam Telerman, Paris (FR)

(73) Assignee: Molecular Engines Laboratories, Paris (FR)

( * ) Notice: Subject to any disclaimer, the term of this patent is extended or adjusted under 35 U.S.C. 154(b) by 0 days.

(21) Appl. No.: 09/762,248

(22) PCT Filed: Jul. 26, 1999

(86) PCT No.: PCT/FR99/01828

§ 371 (c)(1),
(2), (4) Date: Feb. 13, 2001

(87) PCT Pub. No.: WO00/07438

PCT Pub. Date: Feb. 17, 2000

(30) Foreign Application Priority Data

Aug. 5, 1998 (FR) .......................................... 98 10076

(51) Int. Cl.[7] .............................................. G01N 33/00
(52) U.S. Cl. ................................ 800/3; 800/18; 800/21
(58) Field of Search .................................. 800/3, 9, 18

(56) References Cited

FOREIGN PATENT DOCUMENTS

| WO | 92 11874 | 7/1992 |
| WO | 95 09916 | 4/1995 |
| WO | 95 19367 | 7/1995 |

OTHER PUBLICATIONS

Wadhwa et al. J. Biol. Chem. 2002. 277(39) 36665–36670.*
Resnick et al. Proc. Nat'l. Acad. Sci. 2003. 100(17)9934–9939.*
McGaugh et al., Science, 2000. v287: 248–251.*
John Archer, School of Biological Sciences, University of Sussex, Falmer, Brighton, Sussex, England, *Tests for Emotionality in Rates and Mice: A Review*, Behav., 1973, 21, pp. 205–235.
Roger N. Walsh—Department of Psychiatry and Behavioral Sciences, Stanford University and Robert A. Cummins—Department of Physiology, University of Queensland, Brisbane, Australia, *The Open–Field Test: A Critical Review*, Psychological Bulletin, 1976, vol. 83, No. 3, pp. 482–504.
Richard G. M. Morris—University of St. Andrews, St. Andrews, Fife, United Kingdom, *Spatial Localization Does Not Require the Presence of Local Cues*, Learning and Motivation 12, 1981, pp. 239–260.
Richard G. M. Morris—MRC Cognitive Neuroscience Group, Psychological Laboratory, University of St. Andrews, St. Andrews, Fife United Kingdom, *Developments of a water–maze Procedure for Studying Spatial Learning in the Rat*, Journal of Neuroscience Methods, 11, 1984, pp. 47–60.

(Continued)

Primary Examiner—John L. LeGuyader
Assistant Examiner—James Douglas Schultz
(74) Attorney, Agent, or Firm—Foley & Lardner LLP (57) ABSTRACT

Mice that are deficient in p53 are found to have memory disorders and/or behavioral disorders such as increased anxiety. A method of using p53-deficient mice to screen compounds for memory restoring activity and/or anti-anxiety activity is described.

7 Claims, 5 Drawing Sheets

OTHER PUBLICATIONS

Karen Hsiao, Paul Chapman, Steven Nilsen, Chris Eckman, Yasuo Harigaya, Steven Youkin, Fusheng Yang, Greg Cole, *Correlative Memory Deficits, AβElevation, and Amyloid Plaques in Transgenic Mice*, Science, vol. 274, Oct. 4, 1996, pp. 99–102.

J. Nalbantoglu, G. Tirado–Santiago, A. Lahsaïnl, J. Poirier, O. Goncalves, G. Verge, F. Momoll, S. A. Weiner, G. Massicotte, J.P. Jullen, M. L. Shapiro, Departments of Neurology & Neurosurgery, Psychology, Psychiatry, McGill Centre for Studies in Aging, McGill University, Montreal, Quebec H3A 2B4, Canada, Montreal Neurological Institute, Montreal, Quebec H3A 2B4, Canada, Université du Québec á Trois–Riviéres, Trois–Riviéres, Quebec G9A 5H7, Canada, and Centre for Neuroscience, Montreal General Hospital, Montreal, Quebec H3G 1A4, Canada, *Impaired Learning and LTP in Mice Expressing the Carboxy Terminus of the Alzheimer Amyloid Precursor Protein*, Nature, vol. 387, May 29, 1997, pp. 500–505.

Pierre Morméde, D.V.M., Ph.D. Laboratoire de Neurogéné-tique et Stress, INSERM–U471–INRI–Institut Francois Magendie, Bordeaux, France, and Byron C. Jones, Ph.D. (Editor), Department of Biobehavioral Health and Pharmacology, College of Health and Human Development, The Pennsylvania State University, University Park, Pennsylvania, *Neurobehavioral Genetics Methods and Applications*, Chapter 22, Genetics and Emotional Behaviors—Experimental Studies, Pierre Mormede and Andre Ramos, CRC Press 2000, p. 301–315.

R.T. Gerlai (Editor), South San Francisco, CA, and W.E. Crusio (Editor), Orléans, France, *Evaluating Anxiety in Rodents*, Techniques in the Behavior and Neural Sciences—Handbook of Molecular–Genetic Techniques for Brain and Behavior Research, Jacqueline N. Crawley, vol. 13, Elsevier 1999, Chapter 4.6, pp. 667–673.

Jean Michel Lassalle and Douglas Waiilsten, Laboratoire d'Ethologie et de Psychophysiologie, Univesite Francois Rabelals, Parc de Grandmont, 37200 Tours, France, and Deparmtne of Pschology, University of Alberta, Edmonton, Alberta, Canada, T6G 2E9, D. Goldowitz (Editor), Memphis, Tennessee, USA, D> Wahlsten (Editor), Edmonton, Alberta, Canada, R>E> Wimer (Editor) Duarte, California, USA, *Behavioral Paradigms: General Procedures and Spatial Memory*, Techniques for the Genetic Analysis of Brain and Behavior: Focus on the Mouse, Chapter 22, Elsevier 1992, pp. 391–406.

Pierre Morméde, D.V.M., Ph.D. Laboratoire de Neurogéné-tique et Stress, INSERM–U471–INRI–Institut Francois Magendie, Bordeaux, France, and Byron C. Jones, Ph.D. (Editor), Department of Biobehavioral Health and Pharmacology, College of Health and Human Development, The Pennsylvania State University, University Park, Pennsylvania, *Neurobehavioral Genetics Methods and Applications*, Chapter 9, Behavioral Phenotyping of Transgenic and Knockout Mice, Jacqueline N. Crawley, CRC Press 2000, p. 105–119.

Jacqueline N. Crawley, Ph.D., *What's Wrong with My Mouse? Behavioral Phenotyping of Transgenic and Knockout Mice*, Chapter 6, Learning and Memory, Wiley–Liss 2000, pp. 83–95.

V. Sah et al., Nature Genetics, vol. 10, "A subset of p53–deficient embyros exhibit exencephaly," pp. 175–180 (1995) XP002101318.

JP Roperch et al., Nature Medicine, vol. 4, No. 7, "Inhibition of presenilin 1 express is promoted by p53 and p21–WAF1 and results in apoptosis and tumor suppression," pp. 835–838 XP002122379.

YH Jiang et al., Neuron, vol. 21, No. 4, "Mutation of the Angelman ubiquitin ligase in mice causes increased cytoplasmic p53 and deficits of contextual learning and long–term potentiation," pp. 799–811 (1998) XP002122380.

XP–002101319—Howard K. Gershenfeld et al.: "Mapping Quantitative Trait Loci for Fear–like Behaviors in Mice," Genomics 46, pp. 1–8 (1997) Academic Press.

* cited by examiner

USE OF ANIMAL MODEL DEFICIENT IN P53 AND HAVING MEMORY DEFICIENCY AND/OR BEHAVIORAL DISORDERS FOR THERAPEUTIC PURPOSES

The present invention relates to an animal model having anxiety-related memory deficiency and/or behavioral disorders. It also relates to the use of this animal model for the screening and characterization of molecules capable of acting on memory and/or anxiety. It also proposes the use of a compound or a composition for the preparation of a medicament intended for said treatments.

The inventors have indeed established a relationship between a functionality defect in the molecular pathway of the p53 gene, on the one hand, and anxiety-related memory and/or behavioral disorders, on the other hand.

While the role of the p53 gene as tumor suppressor has been well established by a series of studies (Levine et al., 1991; Eliyahu et al., 1989; Michalovitz et al., 1990; Hollstein et al., 1991), the investigations on p53-deficient mice which succumb rapidly to neoplasia have contributed toward reinforcing this observation (Donchower et al., 1992). Interestingly, at a specific level of their development, a significant portion of these mice show major impairments including the abnormal closure of the neural tube (Sah et al., 1995; Armstrong et al., 1995) leading to exencephaly and then anencephaly.

The inventors therefore focused on studying mice having a deficiency in their p53 gene but born with an unimpaired central nervous system (CNS). No previous study has described any flagrant histopathological abnormality; however, this does not exclude the possibility that the nonfunctional p53-gene may-influence, at a molecular level, the transduction pathways giving rise to an abnormal functioning of central nervous system.

The inventors therefore focused on determining if mice homozygous or heterozygous with respect to the deficiency of their p53 gene showed any characteristic feature in their neurological and cognitive behavior.

Two groups of animals were studied, homozygous young mice p53−/− (that is to say in which the two alleles of the p53 gene are not functional) and heterozygous adult mice p53−/+ (in which only one of the two alleles of the p53 gene is not functional). This choice was dictated by the fact that the homozygous mice p53−/− (or so-called "knock-out" mice) develop tumors at an early stage of their life while the heterozygous mice develop tumors much later. The experiments were therefore carried out over a period of time when the animal is not ill since mice carrying tumors can have abnormal behavior which does not result from a neurological dysfunction but rather from the fact that they are suffering from their tumors. The mice deficient in their p53 gene and used in the context of the present invention are marketed by TACONIC FARMS, USA.

Two tests presented in detail below were carried out, namely the Morris swimming pool and the Open-Field.

The Morris swimming pool test (Morris et al., 1981, Morris et al., 1984), in which spatial learning and memory are evaluated, was used successfully in recent studies in particular on model mice having symptoms of Alzheimer's disease (Nalbantoglu et al., 1997, Hsiao et al., 1996).

In the Open-Field test, behavioral parameters are measured. (Archer et al., 1973, Walsh et al., 1976). This procedure has already been used in the context of the evaluation of the psychological profile of mice having a behavior associated with fear (Gershenfeld et al., 1997) and to study the effects on behavior of the inactivated gene encoding the estrogen receptor-(Ogawa et al., 1997).

These tests were carried out according to a "blind" design as regards the age and the genotype of the mice.

FIGS. 1a and 1b relate to homozygous young mice p53−/− and FIGS. 1c and 1d relate to heterozygous adult mice p53−/+. In both cases, the spatial bias index is calculated immediately after learning the procedural component of the test and then fifteen days later without additional training.

FIGS. 2a and 2c present the number of crossings of the central sector by the p53−/− and p53−/+mice, respectively, compared with the control mice. FIGS. 2b and 2d represent the percentage of the number of crossings of the central sector relative to the total number of crossings for the same groups of mice.

FIGS. 1e and 2e relate to the analysis of variance (ANOVA) by means of a diagram of repeat measurements, relating to the behavior of the mice. The square correlation ($r^2$) was calculated in order to explain the part of the variance resulting from the deficiency of the p53 gene.

FIG. 3 also presents the results obtained by the Morris swimming pool test as a function of the sex of the mice. Once in the water, the mice have to learn to navigate toward the invisible platform. At the end of the learning, the mice are subjected to the spatial bias index test (F=female, M=male, WT=wild type). The two modes of variance analysis revealed a significant interaction of the genotypic sex ($F(1.43)=11.63$; $p=0.001$; $r^2=0.26$). Scheffépost-hoc test: Fp53−/− versus FWT=3.25; $p=0.01$; Fp53−/− versus Mp53−/−=2.77; $p=0.043$.

The Northern-blot analysis (a–f) of Wafl, PS1 and GAPDH (as control) is carried out on brains of young (a–c) and adult (d–f) mice. Lane 1 corresponds to the control mouse, lanes 2–3 to the male and female p53 knock-out mice. (a–c) correspond to the same Northern blot hybridized with different probes. No difference was noted in the expression of Wafl and of PS1 between the control and the knock-out mice. For the adult mice, the hybridization is also carried out on the same Northern blot (d–f). The parentheses for (GAPDH) and (PS1) indicate what remains of the probes after dehybridization under nonstringent conditions. A high induction of p21 Wafl (d) and a repression of PS1 (e) are noted in the p53-deficient mice.

The Western-blot analysis is carried out on protein extracts from the brains of the same adult animals (g–i), with anti-Wafl, anti-PS1 and anti-beta-tubulin (as control) antibodies. Lane 1 corresponds to the control mouse; lanes 2–3 to the p53 knock-out mice. An increased expression of p21Wafl and a reduced expression of PS1 are observed in the p53-deficient mice.

(a) and (b) represent labeling of the isocortex with hematoxylin and with eosin in a control mouse and a knock-out mouse, respectively. The arrows indicate a thinning of the isocortex in the knock-out mouse (b). The magnification is 6.6 relative to the origin.

(c) and. (d) represent staining by the TUNEL technique and the Harris hematoxylin counterstaining in the control (c) and in the knock-out mouse (d). In (d), two positive nuclei are observed by the TUNEL technique (arrows). The magnification is 132.

(e) illustrates the quantification by the TUNEL technique.

(f–i) illustrate the immunohistochemical analysis using anti-amyloid-beta 42 specific antibodies f and h correspond to the control mice, g and i are p53 knock-out mice which show an intracytoplasmic accumulation of amyloid-beta 42 (f–g: magnification×40, h–l magnification ×100).

Results of the Morris Swimming Pool Test

Figure 1:
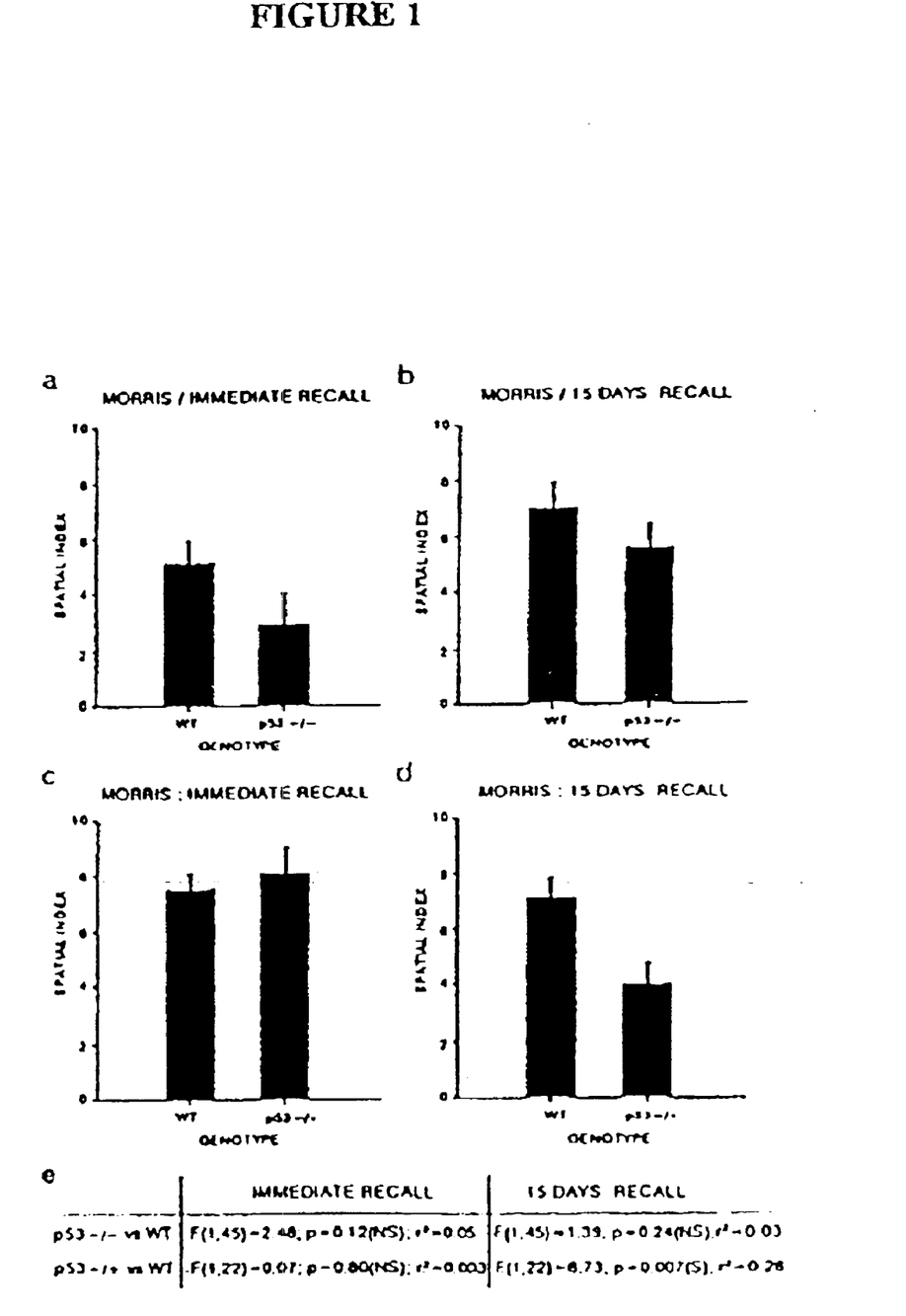
FIG. 1 presents results obtained by the Morris swimming pool test. It presents the spatial bias index as a function of the genotype of the mice.

The young mice p53–/– and the adult mice p53–/+satisfy the test in a manner comparable to the control mice of the same age. This indicates that spatial learning in these mice is not affected by any deficiency in their p53 gene (FIG. 1a and FIG. 1c). In order to measure the memory of these mice, they were again subjected to the Morris swimming pool test after a period of two weeks and without additional training. The young mice p53–/– have a lower spatial index but not significantly different from that shown by the control mice at the same age (FIG. 1b). On the other hand, the adult mice p53–/+ have a significantly lower spatial index than that shown by the control mice (FIG. 1d).

These results show that a memory deficiency is present in this group of animals since the real level of the spatial index, after a period of fifteen days, depends only on their capacity to recall the test. A histological examination of the brain of the adult mice p53–/+ was carried out but did not reveal any abnormality (data not shown). The fact that this memory deficiency is only visible in the adult mice p53–/+ and not in the young mice p53–/– suggests that an age-dependent factor, that is to say the stage of maturation of the brain, may play a role in the detection of memory deficiency. Although most studies of this type designed to detect behavioral or memory abnormalities, in neurodegenerative diseases, are carried out on adult mice, adult homozygous mice could not be studied because of the tumor development and that is the reason why the study was carried out on heterozygous mice.

Results of the Open-Field Test

Figure 2:
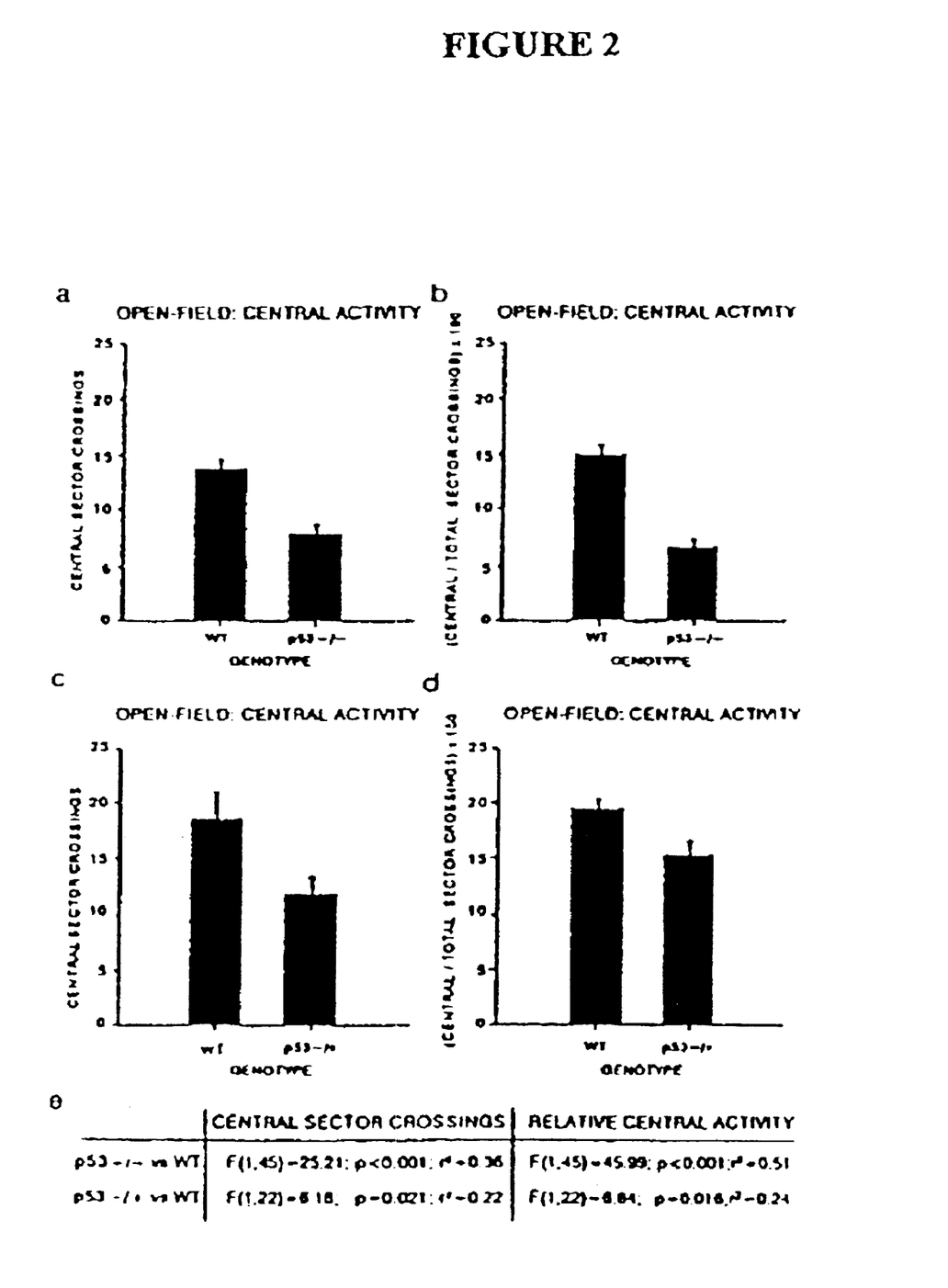
FIG. 2 presents the results obtained by the Open-Field test consisting in counting the number of times the mouse crosses the central part of the field knowing that the anxiety which it can manifest is capable of preventing it from doing so.

The young mice p53–/– (FIG. 2a) and adult mice p53–/+ (FIG. 2c) show a significantly lower number of crossings of the central sector compared with the control group of mice of the same age. Since the number of crossings of the central sector is proportional to the capacity of the mice to overcome their fear of moving away from the wall, in order to explore an unknown territory, these results suggest that the p53-deficient mice are more thigmotaxic than the corresponding normal mice (that is to say that they have a higher tendency to keep close to the walls). In order to exclude the possibility that a small number of crossings of the central sector may be due to a globally reduced locomotive activity, the number of crossings of the central sector was expressed as a percentage of the total number of crossings. This relative central activity is also significantly reduced in the two groups of p53-deficient mice (FIG. 2b and FIG. 2d).

Figure 3:
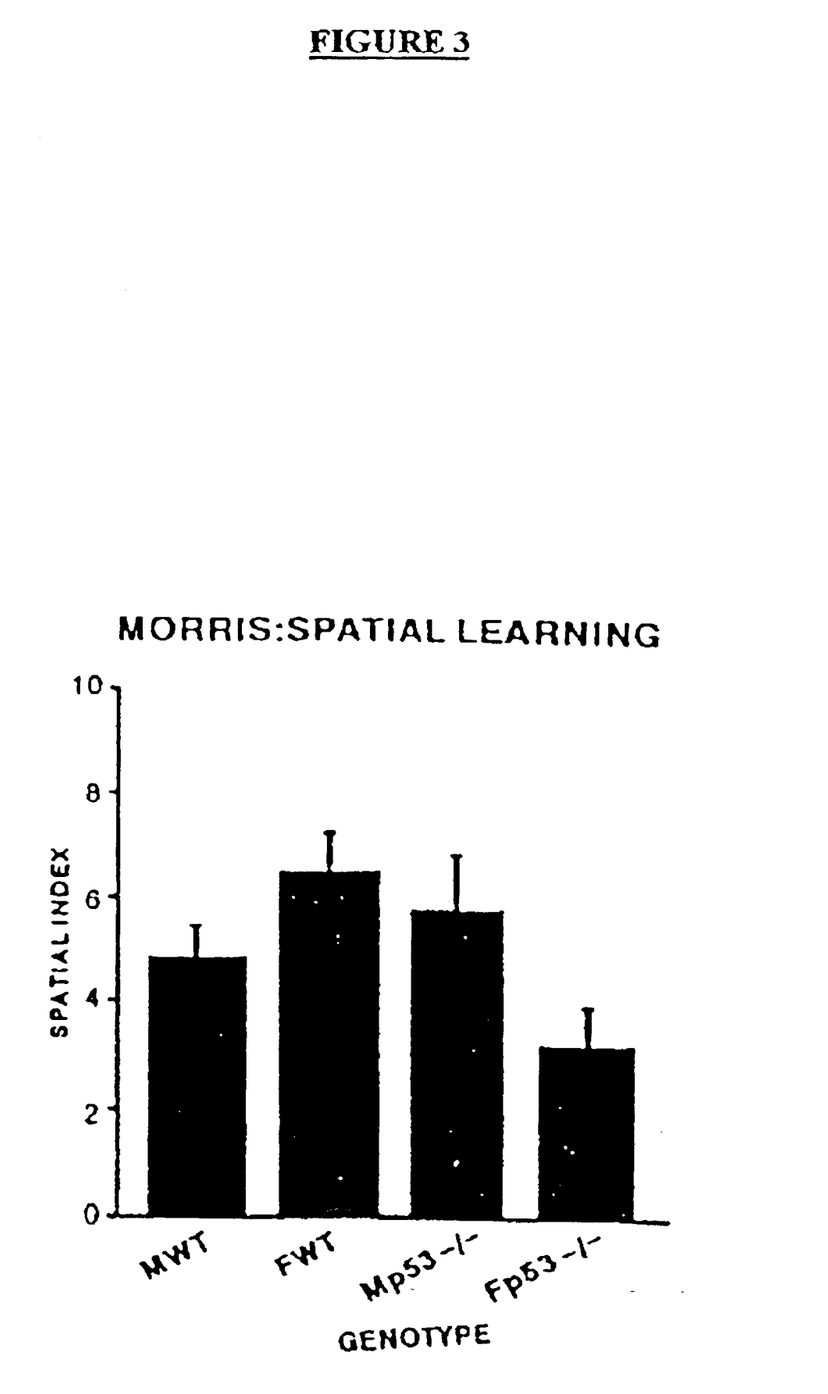

The inventors then focused on going deeper into the results of the Morris swimming pool tests as reported above, obtained for the homozygous mice p53–/–, according to their sex. They therefore separated the measurements of the spatial index obtained for the male mice from those obtained for the female mice and compared them to the corresponding control group (FIG. 3).

While the males p53–/– show no significant difference from the male and female wild-type controls, the females p53–/– show a performance which is significantly less than the control, this indicating lower capacities to memorize and a poorer spatial learning.

Figure 4:
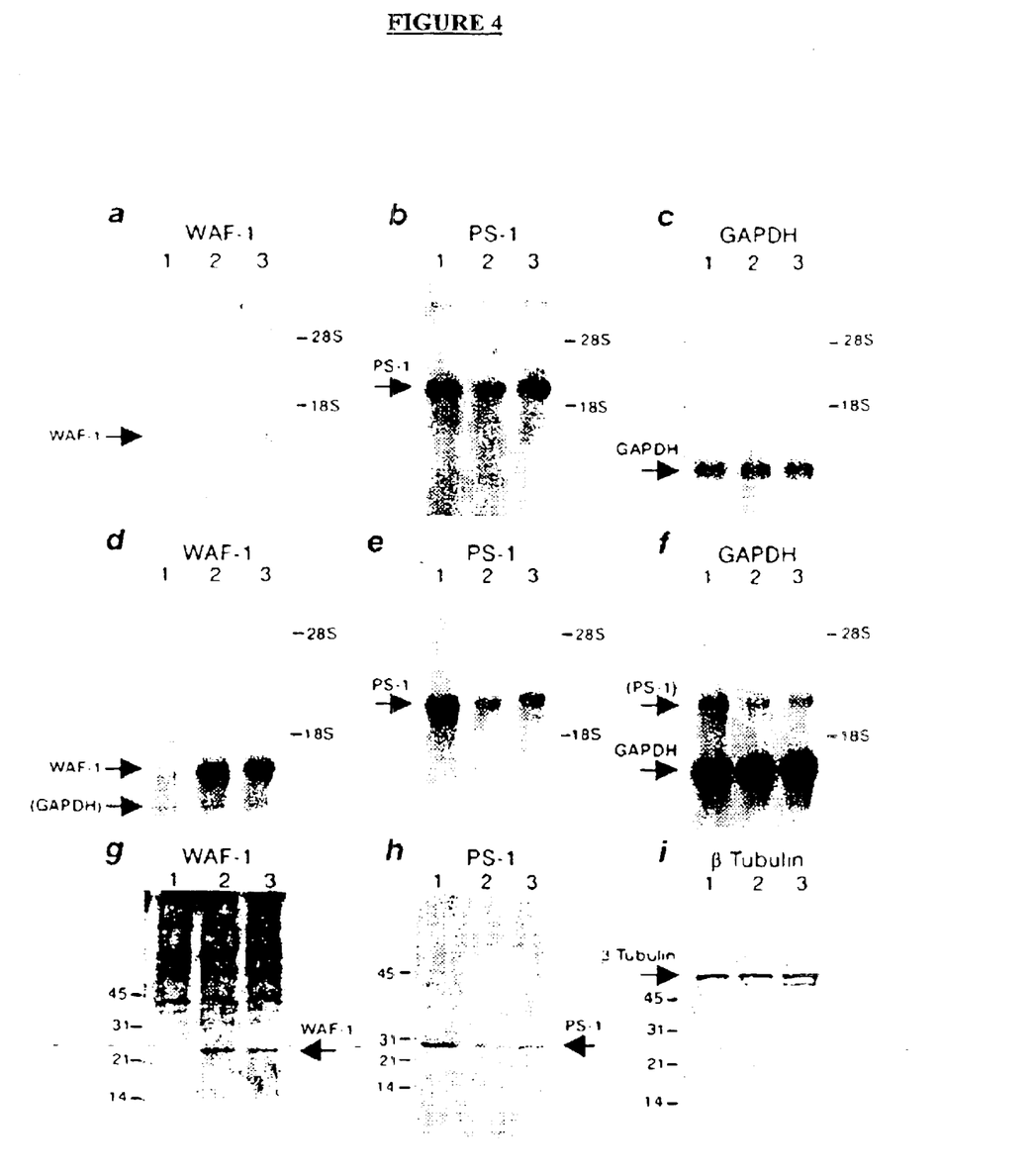
FIG. 4 illustrates the activation of p21Wafl and the repression of PS1 in the brain of adult mice p53−/− (this includes mice p53−/− that have while young performed the Morris swimming pool and Open-Field tests as reported above. Upon analysis, it was found that these mice had not yet developed tumors).

The inventors then continued their investigations in order to determine if the disruptions in the functions of the central nervous system in the p53 knock-out mice were correlated with changes in the expression, in the brain, of p21Wafl and PS1 since these two genes are regulated by wild-type p53 and are considered as modulators of apoptosis. They detected striking differences correlated with age. The young mice p53–/– (two months old) have the same level of mRNA corresponding to p21Wafl and PS1 as the control mice (FIGS. 4a–c). By contrast, the adult mice p53–/– (the same group on which the Morris swimming pool and Open-Field tests were carried out two months earlier) show a high increase in the expression of p21Wafl and high repression of the expression of PS1 (FIGS. 4d–f). Given the fact that PS1 undergoes proteolytic cleavage, the inventors tested its expression at the protein level. As shown in FIG. 4h, the expression of the PS1 protein is very substantially reduced in the p53 knock-out mice. The inventors also tested the p53 knock-out mice in relation to mutations in the coding region of the cDNA for PS1. Nothing was found. These observations suggest that the older p53 knock-out mice overcompensate for the loss of p53 by over-expression of p21Wafl with consequently a repression of PS1. Previous studies by the inventors showed that the increased, expression of p21Wafl resulted from the repression of PS1 with an induction of apoptosis and that the inhibition of the production of PS1 by an antisense cDNA induced apoptosis. This corroborates the notion that the reduction in the expression of PS1 in the brain could cause impairments in the functioning of the central nervous system through an increase in apoptosis.

The fact that young p53 knock-out mice already have deficiencies in relation to learning, memory and behavior before a measurable reduction in the expression of PS1 is similar to what is found in neurodegenerative diseases. Abnormalities in behavior may be observed in patients who have been suffering from Alzheimer's disease for a long time before the terminal stage of the disease in which there is neurodegeneration. These data suggest a process which progresses slowly, in which the memory and behavioral abnormalities take place before a repression of PS1 becomes measurable.

Figure 5:
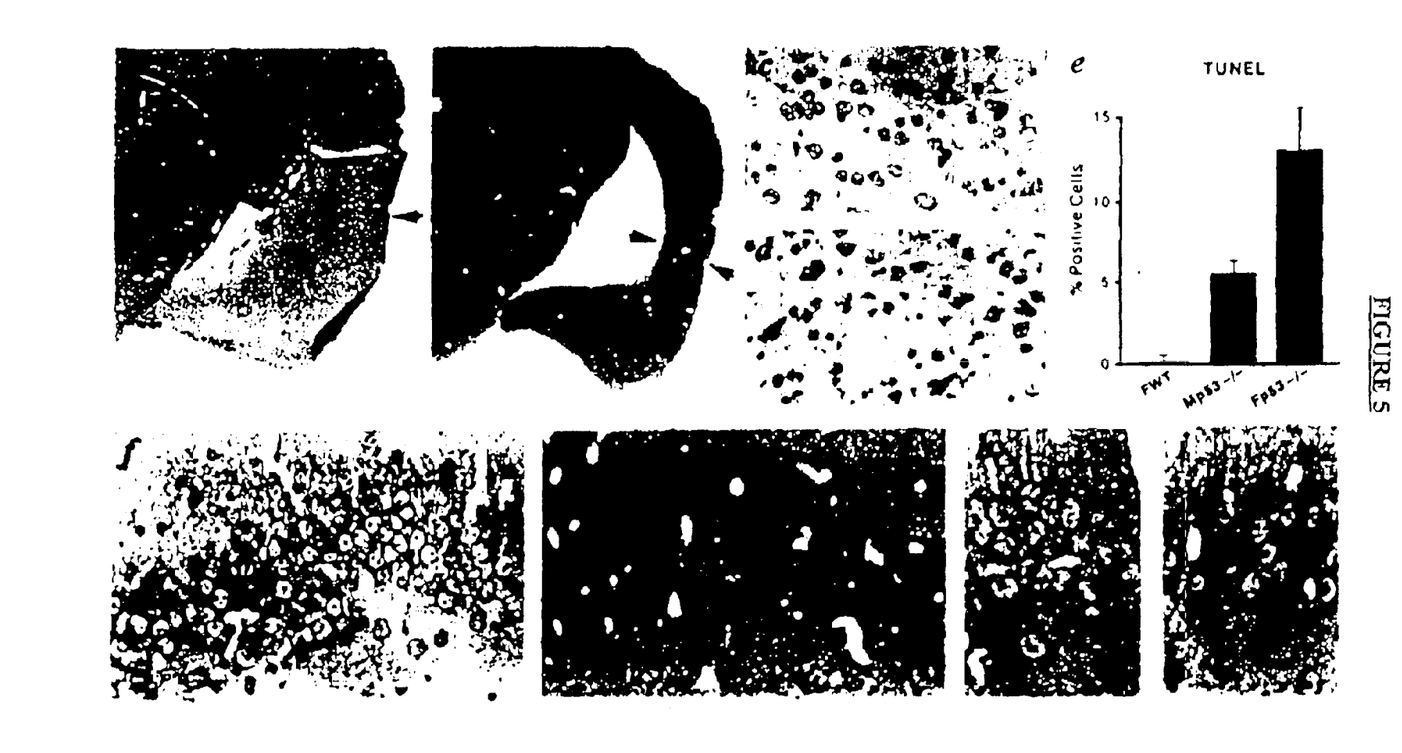
FIG. 5 illustrates apoptosis and the intracytoplasmic accumulation of amyloid-beta 42 in the brains of adult mice p53−/− as defined above.

The histopathological analyses combined with the TUNEL technique for evaluating apoptosis were performed on the same group of old animals showing a reduction in the expression of PS1 as indicated above. Three of the four mice showed no striking pathological abnormality. One knock-out mouse (female) showed a thinning of more than 50% of the isocortex with a very enlarged ventricle compared with the control animals (FIGS. 5a–b). The TUNEL experiment showed discrete apoptotic lesions (FIG. 5d) in the brain without massive apoptosis. The quantification of the positive cells by TUNEL (FIG. 5e) indicated that, whereas in the control brains only one case showed five positive cells out of 1740 counted, the mice p53–/– had up to 5.5% ($25/465$) and 13% ($39/305$) positive cells by TUNEL in the male and female animals, respectively (FIG. 5e).

Because patients with Alzheimer's disease and transgenic mice with mutations in PS1 show neurodegeneration with apoptosis and accumulation of amyloid-beta 42, the inventors then tested for the presence of amyloid-beta 42 in the brains of the p53 knock-out mice. As shown in FIGS. 5h–i, the p53-deficient mice show high levels of amyloid-beta 42 in the cytoplasmic compartment.

In conclusion, these experiments indicate that the intact expression of p53 is necessary to ensure the complex functions of the central nervous system. These functions include memory and a standard behavior in anxiogenic situations. The precise mechanism by which the loss of the functionality of p53 interferes with memory and behavior may be due to a deregulation of the p53 metabolic pathway at the molecular level.

Furthermore, it was shown that the mice p53−/− which showed deficiencies in memory, in their ability to learn, as well as an abnormal behavior had discrete apoptotic lesions in their brain. These impairments appear to indicate an age-dependent overcompensation of the p53 deficiency in the long term by an increase in the expression of p21Wafl which leads to a repression of PS1. This in turn compromises the anti-apoptotic effect of PS1. These data indicate that the loss of the function of PS1 either through mutations as shown in early familial Alzheimer's diseases, or through the deregulation of expression as is the case in p53-deficient mice, activates no the program of cell death. This is coupled with the impaired metabolism of APP (Amyloid Precursor Protein) leading to the accumulation of amyloid-beta 42. Thus, the inventors have demonstrated the basis for novel strategies for the treatment of neurodegenerative diseases.

Thus, surprisingly, the inventors have demonstrated that a mouse deficient in its p53 gene had learning and memory disorders and/or behavioral disorders such as anxiety.

Consequently, the present invention relates to an animal model, and in particular a mouse, having memory deficiency, the animal in question having at least one of the alleles of its p53 gene nonfunctional. This is the case with the mice p53−/+.

The model in question may in addition have behavioral disorders such as anxiety, and in this case, it is both alleles of the p53 gene in the animal which are not functional. This is the case with the homozygous mice p53−/−, but also as indicated above, the mice p53−/+ which also have behavioral disorders in an anxiogenic situation.

Thus, the animal model in question may be used for the screening of molecules capable of having an anxiolytic activity and/or of at least partially restoring memory.

Indeed, after having subjected mice p53−/+ to any learning test, it is known that two weeks later, they show a memory deficiency. They are then treated with a molecule (preferably suspected of acting on the memory), and the treated mice are again subjected to the test. The molecule will only be selected for additional investigations if it made it possible to significantly restore the memory of said mice.

In the context of tests conventionally carried out in this field, the animal model in accordance with the invention may also be used to determine the characteristics of a molecule which is known to be capable of acting on anxiety and/or memory, the characteristics relating to the pharmacodynamics, the pharmacokinetics and the toxicity of these molecules and the like.

Finally, the present invention also relates to the use of an agent that induces the metabolic pathway of the p53 gene, whether upstream or downstream thereof, for the preparation of a medicament intended for the treatment of memory and anxiety disorders and/or of neurodegenerative diseases. Indeed, the p53 gene is involved in a cascade of genes which interact with each other. The equilibrium of this cascade is characteristic of "a normal state" characterized by control of cell growth and of the process of apoptosis. It may therefore be advantageous to be able to act at different levels of the molecular pathway of the p53 gene according to the desired result.

Consequently, the present invention also relates to the case where said induction of the metabolic pathway of the p53 gene is an induction of the expression of a gene activated or inhibited by the p53 gene.

In particular, the abovementioned agent may in addition exhibit an antitumor activity by activation of the metabolic or molecular pathway of the p53 gene. This agent may be for example the product of the expression of one of the genes involved in the cascade mentioned above.

The invention is not limited to the above description and the results obtained in the context of the abovementioned experiments will be understood more clearly by means of the presentation below of the two tests to which the mice were subjected.

Methods: Behavioral Measurements

The Morris Swimming Pool (Morris, 1981)

The circular swimming pool made from PVC, of ivory color and 70 cm in diameter and 30 cm in height, is filled with water at 22±1° C., which is colored white by addition of the coloring Opacifier 631®, to a height of 12 cm below the edge of the wall. A circular platform 5 cm in diameter serving as the objective is immersed 0.5 cm under the water, 7 cm away from the wall. The device is placed in a rectangular room. Two rectangular markers (50×30 cm), one black and one with black and white stripes, are attached to two adjacent walls 1.5 meters away from the swimming pool. A video camera, placed vertically above the swimming pool makes it possible to record the movements of the mice on a video tape in order to analyze them subsequently. The experimentalist is hidden behind a white curtain. Placed in the water, facing the wall, in a quadrant that varies in a pseudorandom manner from one test to another, the mice have to learn to navigate toward the platform using the distal visual markers available in the room. After a practice session of three trials intended for learning the procedural component of the test, the mice are subjected to three consecutive trials per day for 4 days. The maximum time allowed to reach the platform was set at 60 seconds. If a mouse cannot reach the platform within this period of time, it is guided to it by the experimentalist. The sum of the three lag times constitutes the score for the session. After the last trial of the third session, the mouse is subjected to a spatial bias test intended to check the accuracy of the spatial learning (short-term memory). The platform is then removed from the device and the mouse, starting from the opposite quadrant, has to swim in search of it for one minute. The route is recorded on a videotape and a spatial bias index is then calculated. It corresponds to the difference between the number of times it crosses an 8 cm ring surrounding the position of the platform and the mean number of times it crosses the three annuli placed symmetrically in the other three quadrants. Another spatial bias test is carried out after a period of 15 days without additional training (long-term memory).

Open-field (Archer, 1973; Walsh and Cummins, 1976)

The mice are introduced individually into a grey PVC cylinder 40 cm in diameter and 30 cm in height, placed on a sheet of white paper through which it is possible to distinguish the lines which divide the floor of the open-field into 7 sectors having the same surface area (1 central sector and 6 peripheral sectors). This device, illuminated with white light diffusing through frosted glass (125 lux) constitutes for the mice a moderately anxiogenic situation. The mice are subjected to three daily sessions of 15 minutes, 45 minutes apart, this being for 4 consecutive days. The behavioral measurements are performed for the first 5 minutes of each session. They consist essentially in counting the number of times the mice "are bold enough" to move away from the side walls of the cylinder in order to cross the central sector of the Open-Field.

REFERENCES

Amson, R. et al. *Proc. Natl. Acad. Sci. USA* 93, 3953–3957 (1996)
Archer, J. *Animal Behaviour* 21, 205–235 (1973)
Armstrong, J. F., Kaufman, M. H., Harrison, D. J. and Clarke, A. R. *Curr. Biol.*, 5, 931–936 (1995)
Chapillon, P. and Roullet, P. *Developmental Psychobiology* 29, 529–545 (1996)
Donchower, L. A. et al. *Nature* 356, 215–221 (1992)
Eliyahu, D., et al. *Proc. Natl. Acad. Sci. USA* 86, 8763– (1989)
Gershenfeld, H. K. and Paul, S. M. *Genomics* 46, 1–8 (1997)
Hollstein, M., Sidransky, D., Vogelstein, B., Harris, C; C. *Science* 253, 49–53 (1991)
Hsiao, K. et al *Science* 274, 99–102 (1996)
Levine, A. J., Momand, J. and Finlay, C. A., *Nature* 351, 453– (1991)
Michalovitz, D., Halevy, O. and Oren, M. *Cell* 62, 671– (1990)
Morris, R. G. M. *Learning & Motivation* 12, 239–260 (1981)
Morris, R. G. M. *J. Neurosci. Meth.* 11, 47–60 (1984)
Nalbantoglu, J. et al. *Nature* 387, 500–505 (1997)
Nemani, M., et al. *Proc. Natl. Acad. Sci. USA* 93, 9039–9042 (1996)
Ogawa, S., Lubahn, D. B., Korach, K. S. and Pfaff, D. W. *Proc. Natl. Acad. Sci. USA* 94, 1476–1481 (1997)
Roperch J. P., Alvaro V., Prieur S., Tuynder M., Nemani M., Lethrosne F., Piouffre L., Gendron M. G., Israeli D., Dausset J., Oren M., Amson R., and Telerman A. Inhibition of Presenilin 1 expression is promoted by p53 and p21WAF-1 and results in apoptosis and tumor suppression. *Nature Medicine* 1998; 4: 835–838
Sah, V. P. et al. *Nat. Genet.* 10, 175–180(1995)
Walsh, R. N. and Cummins, R. A. *Psychological Bulletin* 83, 482–504 (1976).

What is claimed is:

1. A method for identifying compounds with anti-anxiety activity comprising:
   (a) administering a test compound to a mouse that has at least one native non-functional allele of the p53 gene, wherein the mouse exhibits increased anxiety, and
   (b) determining whether said test compound decreases anxiety in said mouse, in which test compounds that decrease anxiety in said mouse are identified as compounds with anti-anxiety activity.

2. The method of claim 1, wherein the mouse has two native non-functional alleles of the p53 gene.

3. A method for identifying compounds with long-term memory restoring activity, comprising:
   (a) administering a test compound to a mouse that is heterozygous for the p53 gene in that the mouse has one native non-functional allele of the p53 gene, wherein the mouse exhibits a deficiency in long-term memory storage, and
   (b) determining whether said test compound improves the deficiency in long-term memory storage in said mouse.

4. The method of claim 1, wherein determining whether said test compound decreases anxiety in said mouse comprises subjecting said mouse to an Open-Field test.

5. The method of claim 1, wherein determining whether said test compound decreases anxiety in said mouse comprises determining whether said test compound decreases thigmotaxia.

6. The method of claim 3, wherein determining whether said test compound improves the deficiency in long-term memory storage in said mouse comprises subjecting the mouse to a Morris swimming pool test.

7. The method of claim 3, wherein determining whether said test compound improves the deficiency in long-term memory storage in said mouse comprises calculating a spatial bias index.

* * * * *